(12) United States Patent
Barber et al.

(10) Patent No.: US 6,305,226 B1
(45) Date of Patent: Oct. 23, 2001

(54) METHOD AND APPARATUS FOR IMAGING ACOUSTIC FIELDS IN HIGH-FREQUENCY ACOUSTIC RESONATORS

(75) Inventors: Bradley Paul Barber, Chatham; Peter Ledel Gammel, Millburn, both of NJ (US); Rafael Nathan Kleiman, New York, NY (US); Hugo Fernando Safar, Westfield, NJ (US)

(73) Assignee: Agere Systems Guardian Corp., Miami Lakes, FL (US)

( * ) Notice: Subject to any disclaimer, the term of this patent is extended or adjusted under 35 U.S.C. 154(b) by 0 days.

(21) Appl. No.: 09/385,745

(22) Filed: Aug. 30, 1999

(51) Int. Cl.[7] .................................................. G01N 29/00
(52) U.S. Cl. ............................................. 73/606; 73/620
(58) Field of Search ..................... 73/606, 593, 630, 73/620, 105, 618, 579; 250/306, 307

(56) References Cited

U.S. PATENT DOCUMENTS

| | | | |
|---|---|---|---|
| 5,267,471 | * | 12/1993 | Abraham et al. ........................ 73/105 |
| 5,319,977 | * | 6/1994 | Quate et al. ............................. 73/105 |
| 5,381,101 | * | 1/1995 | Bloom et al. ........................... 73/105 |
| 5,503,010 | * | 4/1996 | Yamanaka .............................. 73/105 |
| 5,515,719 | * | 5/1996 | Lindsay .................................. 73/105 |
| 6,006,593 | * | 12/1999 | Yamanaka .............................. 73/105 |

OTHER PUBLICATIONS

T. Hesjedal, E. Chilla, and H.-J. Fröhlich, High resolution visualization of acoustic wave fields within surface acoustical wave devices, Appl. Phys. Lett. 70(11), 1372 (1997).
A. Gruverman, O. Auciello, and H. Tokumoto, Nanoscale investigation of fatigue effect in Pb(Zr,Ti)O$_3$ films, Appl. Phys. Lett. 69(21), 3191 (1996).
J.A. Christman, R.R. Woolcott, Jr., A.I. Kingon, and R.J. Nemanich, "Piezoelectric measurements with atomic force microscopy", Appl. Phys. Lett. 73, 3851 (1998).
W.J. Spencer, "Observations of resonant vibrations and defect structure in single crystals by x–ray diffraction . . . " in "Physical Acoustics, Principles, and Methods V" Ed. W.P. Mason, p. 111–161 (Academic Press, 1968).

* cited by examiner

Primary Examiner—Helen Kwok
(74) Attorney, Agent, or Firm—Fay, Sharpe, Fagan, Minnich & McKee, LLP

(57) ABSTRACT

This invention relates to a method and apparatus for imaging acoustic fields in high-frequency acoustic resonators. More particularly, the invention is directed to a scanning RF mode microscope system that detects and monitors vibration of high frequency resonators that vibrate in the frequency range of approximately 1 MHz to 20 GHz. The system then maps with sub-Angstrom resolution vibration modes of such devices and obtains quantitative measurements of the piezoelectric properties of the materials.

15 Claims, 4 Drawing Sheets

2.09 GHz 2.14 GHz 2.12 GHz 2.16 GHz

METHOD AND APPARATUS FOR IMAGING ACOUSTIC FIELDS IN HIGH-FREQUENCY ACOUSTIC RESONATORS

BACKGROUND OF THE INVENTION

This invention relates to a method and apparatus for imaging acoustic fields in high-frequency acoustic resonators. More particularly, the invention is directed to a scanning RF mode microscope system that detects and monitors vibration of high-frequency resonator devices that vibrate in the frequency range of approximately 1 MHz to 20 GHz. The system then maps vibration modes of such devices to obtain quantitative measurements of the piezoelectric properties of the thin-film materials.

While the invention is particularly directed to the art of imaging acoustic fields in acoustic resonators, and will be thus described with specific reference thereto, it will be appreciated that the invention may have usefulness in other fields and applications. For example, the invention may be used in any application where detection of high frequency movement of small tightly packaged devices is desired.

By way of background, bulk piezoelectric resonators are utilized as frequency references and filters in the 1 MHZ to 400 MHZ frequency range. A common example is the quartz crystal oscillator used in watches. At these low frequencies, these devices are relatively large (several millimeters). Bulk oscillations of such large devices is achieved, resulting in typical mode shapes ranging in size from hundreds of micrometers to several millimeters.

At higher frequencies, (0.9 GHz to 10 GHz) resonators to be used in wireless communication systems are produced by launching Surface Acoustic Waves (SAW) on bulk crystalline piezoelectrics, or by the manufacture of bulk acoustic wave thin film resonators (TFR). In these latter devices, a piezoelectric film having a thickness of approximately a micrometer is used.

While substantial progress has been made in high-frequency filter design and fabrication, the quality factor Q of such devices is undesirably limited to less than 1000, and consequently the power handling is limited by insertion loss to ~33 dBm. To understand this limitation, i.e. whether it stems from fundamental materials properties of the piezoelectric thin films, from device design or from basic physical behavior of the device, it is important to implement techniques that allow for a direct study of the mechanical properties of the device in operation.

Previous state of the art techniques, developed mainly for imaging the mode of vibration of quartz oscillators, are not capable of detecting the vibration modes of high frequency resonators. The techniques used for mapping low-frequency quartz oscillators rely on the large volume of those samples, and the relatively long-range vibration patterns. For example, the X-ray imaging technique used in quartz oscillators requires a sample volume of at least a cubic millimeter, and resolves vibration patterns of more than one millimeter. On the other hand, in high-frequency acoustic resonators, the vibration of the device is produced over a few cubic micrometers.

More specifically, "Observation of resonant vibrations and defect structure in single crystals by x-ray diffraction topography", W. J. Spencer, in "Physical Acoustics, Principles and Methods", edited by Warren P. Mason, volume V, pages 111–161, Academic Press (1968), gives a detailed presentation of the many X-ray based methods to observe vibration in quartz oscillators. In general, these methods require relatively large oscillators, since as in most scattering techniques, the sensitivity of x-ray diffraction methods improves with large sample volume. Typically, the quartz oscillators studied in this reference had lateral dimensions of 15 mm, and thickness of several mm. The requirement of large sample volume renders this technique inadequate for the imaging of vibration modes of thin film resonators.

In addition, "Piezoelectric measurements with atomic force microscopy, J. A. Christman, R. R. Woolcott, Jr., A. I. Kingon, and R. J. Nemanich, Applied Physics Letters, volume 73, pages 3851–3853 (1998), presents measurements of the piezoelectric coefficient of various thin film materials. These measurements are performed by using an AFM-based technique. Christman et al., however, do not modulate the amplitude of the drive voltage and do not use a phase-locked loop operating at the modulating frequency. As a result, the Christman et al. method is limited to the low frequencies allowed by their cantilever arm. All the results reported by Christman et al. were obtained at 1 kHz. This limitation renders this technique inadequate for the measurement of piezoelectric properties of materials at high frequencies and for the observation of the vibration modes of high frequency devices.

"High resolution visualization of acoustic wave fields within surface acoustic wave devices", T. Hesjedal, E. Chilla, and H.-J. Frölich, Applied Physics Letters, volume 70, pages 1372–1374, presents an AFM-based technique to image the vibration of surface acoustic waves devices. However, the highest frequency of operation demonstrated by Hesjedal et al. is 602.7 MHz, with no claims about the operability of their system at higher frequencies. In addition, Hesjedal et al. claim that the performance of their set-up is intrinsically non-linear. This nonlinear behavior prevents any quantitative measurement.

The present invention contemplates a new method and apparatus for imaging acoustic fields in high-frequency acoustic resonators that resolve the above-referenced difficulties (and others) and achieve desired operation.

SUMMARY OF THE INVENTION

A method and apparatus for imaging acoustic fields in high-frequency acoustic resonators are provided.

In one aspect of the invention, an apparatus is provided that comprises a cantilever arm having a tip disposed at an end thereof—the tip being positioned to touch or come in close proximity to a surface of a specimen, a system to detect motion of the tip, a frequency generator producing a radio frequency signal to excite the specimen—the radio frequency signal having a first frequency that is amplitude modulated at a second frequency where the second frequency is less than the first frequency, a circuit operatively connected between the detector and the frequency generator to synchronize the detector signals with the second frequency, a first processing element operatively connected to the detector to convert the detector signals to first mapping data—the first mapping data relating to physical characteristics of the specimen and a second processing element operatively connected to the detector to convert the detector signals to second mapping data—the second mapping data relating to response characteristics of the specimen excited by the first frequency.

In another aspect of the invention, the tip is translated across the surface of the specimen.

In another aspect of the invention, the first mapping data comprises data relating to a topography of the surface of the specimen.

In another aspect of the invention, the tip moves in opposite vertical directions in response to the radio frequency signal.

In another aspect of the invention, the second mapping data comprises data relating to amplitudes of the movement of the tip.

In another aspect of the invention, coefficients relating to characteristics of the specimen are calculated based on the detector signals.

In another aspect of the invention, the apparatus comprises a means for producing a radio frequency signal to excite the specimen—the radio frequency signal having a first frequency that is amplitude modulated at a second frequency where the second frequency is less than the first frequency, a means for generating response signals indicative of movement of the specimen in response to the radio frequency signal, a means for synchronizing the response signals with the second frequency and, a means for converting the synchronized response signals to mapping data—the mapping data relating to response characteristics of the specimen excited by the first frequency.

In another aspect of the invention, the apparatus further comprises a means for converting the response signals to additional mapping data—the additional mapping data relating to physical characteristics of the specimen.

In another aspect of the invention, the means for synchronizing comprises a lock-in circuit.

In another aspect of the invention, coefficients relating to characteristics of the specimen are calculated based on the detector signals.

In another aspect of the invention, a method for determining characteristics of a specimen comprises steps of producing a radio frequency signal to excite the specimen—the radio frequency signal having a first frequency that is amplitude modulated at a second frequency where the second frequency is less than the first frequency, generating response signals indicative of movement of the specimen in response to the radio frequency signal, converting the response signals to first mapping data—the first mapping data relating to physical characteristics of the specimen, synchronizing the response signals with the second frequency and, converting the synchronized response signals to second mapping data—the second mapping data relating to response characteristics of the specimen excited by the first frequency.

In another aspect of the invention, the method comprises calculating coefficients relating to characteristics of the specimen based on the response signals.

Further scope of the applicability of the present invention will become apparent from the detailed description provided below. It should be understood, however, that the detailed description and specific examples, while indicating various embodiments of the invention, are given by way of illustration only, since various changes and modifications within the spirit and scope of the invention will become apparent to those skilled in the art.

DESCRIPTION OF THE DRAWINGS

The present invention exists in the construction, arrangement, in combination of the various parts of the device, and steps of the method, whereby the objects contemplated are attained as hereinafter more fully set forth, specifically pointed out in the claims, and illustrated in the accompanying drawings in which:

DETAILED DESCRIPTION OF THE INVENTION

Figure 1:
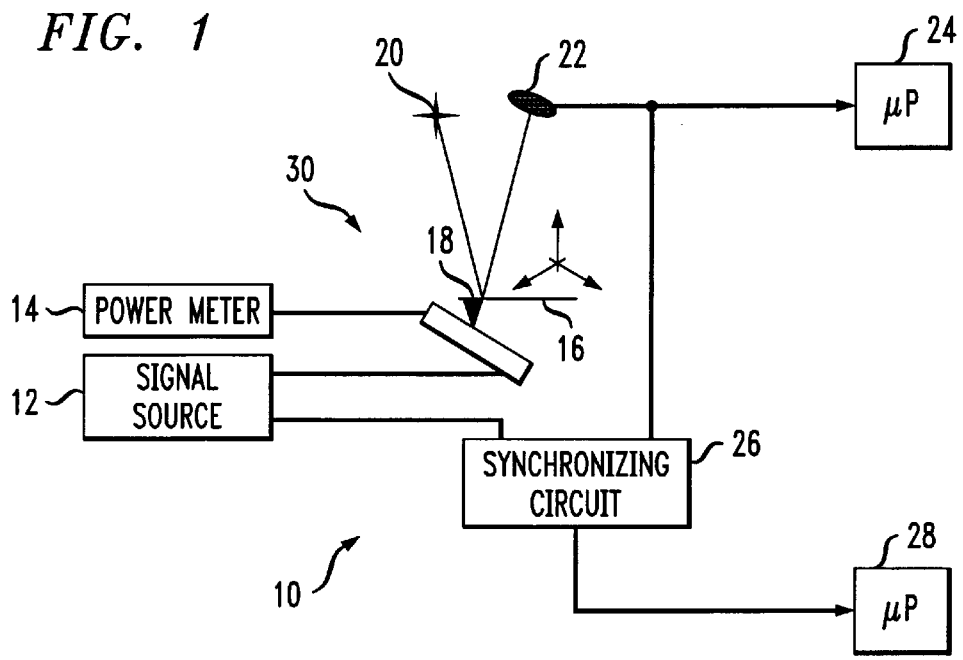
FIG. 1 provides a view of the overall system according to the present invention.

Referring now to the drawings wherein the showings are for purposes of illustrating various embodiments of the invention only and not for purposes of limiting same, FIG. 1 provides a view of an overall system according to the present invention. As shown, the overall system 10 comprises a signal source 12, a power meter 14 that monitors the electrical performance of the system during operation, and a cantilever sensing arm 16 having a tip 18 disposed at an end thereof. It is to be appreciated that an opposite end of the cantilever arm 16 is secured (although not shown) in a suitable manner to allow articulation of the arm 16 and, consequently, the tip 18. The system also includes a light source 20, a light detector 22, a first processing element 24, a synchronizing circuit 26, and a second processing element 28. Also shown in FIG. 1 is a specimen 30 under investigation.

It should be recognized that the system 10 may be housed in a variety of manners to suit the needs and preferences of the users and/or applications of interest. Likewise, components of the system may take a variety of forms to achieve the invention. For example, in one embodiment, the signal source 12 is a radio frequency (RF) signal source that generates a radio frequency signal—on the order of 1 MHz to 20 GHz—that is amplitude modulated at a frequency of approximately 5 KHz and the light source 20 is a laser light beam source.

Also, for the configuration described in connection with FIG. 1, the detection of vertical as well as torsional motion of the tip is achieved through implementation of a system having a laser light source positioned to direct a laser light beam toward the cantilever arm and a detector positioned to detect the laser light beam reflected from the cantilever arm and to produce detector signals based on a position of the reflected beam on the detector. Many alternative techniques, however, such as capacitive and/or piezo-resistive methods, can be used to detect the motion of the cantilever sensing arm and are compatible with the present invention.

The system of FIG. 1 comprises several components well known in the art and typically used in an atomic force microscope (AFM). As such, in operation, an AFM cantilever tip 18 is placed in contact with (or in close proximity to) the specimen or device 30 under investigation. A laser light beam is generated by the light source 20 and directed to be incident on a surface of the cantilever arm 16. The laser beam is then reflected toward the light detector 22. Motion of the cantilever arm 16—caused by movement of the tip 18—is measured as a change in the intensity in the detector that results from consequential movement of the reflected light beam on the detector. The design of the detector 22 is such that it allows for the measurement of the vertical motion of the tip 18 as well as torsional motion of the tip 18. The description herein and examples illustrated are primarily directed to detection of the vertical motion. However, the invention is adaptable to detect torsional motion, as those of skill in the art will appreciate.

As representatively shown by the arrows in FIG. 1, the tip 18 may be translated across the surface of the specimen 30 under investigation. This translation may be produced by the use of gears, stepper motors, piezoelectric drivers, or any combination of those. In one embodiment, motion is achieved by a combination of stepper motors and piezoelectric drivers, allowing for a minimum lateral step of one (1) nanometer and a maximum coverage area of ten (10) square centimeters.

In the low frequency range, known atomic force microscope detection systems operate in a straightforward manner. That is, specimen 30 is vibrated at a low frequency and the tip 18 follows the vibration. As such, the cantilever arm 16 follows the motion of the tip so that the laser light beam that is reflected from the cantilever arm 16 changes its position on the detector 22. This results in detector signals, or response signals, being output by the detector 22 and used by processing elements that are well known in the art, such as processing element 24, to map a physical topography of a surface of the specimen upon which the tip 18 is engaged. This physical topography is known as a DC topography.

However, in frequency ranges higher than approximately 100 kHz, the tip 18 and cantilever arm 16 are mechanically limited and do not follow the motion of the specimen. As such, known solutions fail to satisfy the need to analyze devices in the high frequency range. The present invention provides a solution, however. In this regard, according to the present invention, a radio frequency signal source 12 generates a radio frequency signal having a first frequency in the range of 1 MHz to 10 GHz that is amplitude modulated at a second frequency of approximately 5 kHz.

That is, to investigate the motion of specimens at higher frequencies, the amplitude of the RF voltage applied to the device or specimen is modulated. This modulation is such that it brings the RF amplitude from a maximum to zero, at a frequency that can be followed by the cantilever, e.g. 5 kHz. With the RF on (typically 10 dBm, anywhere in the 10 MHz to 20 GHz frequency range), the maximum amplitude of motion of the specimen is obtained. The cantilever arm 16 is not able to follow the rapid oscillations of the RF frequency; thus it stays at the highest vertical deflection point while the RF frequency is applied. As the amplitude modulation in the 5 kHz range brings the RF amplitude to zero, the amplitude of the device vibrations is also zero, thus the cantilever's position will change. As this sequence is repeated, the cantilever will perform an oscillation at the frequency of the modulation.

Figure 2:
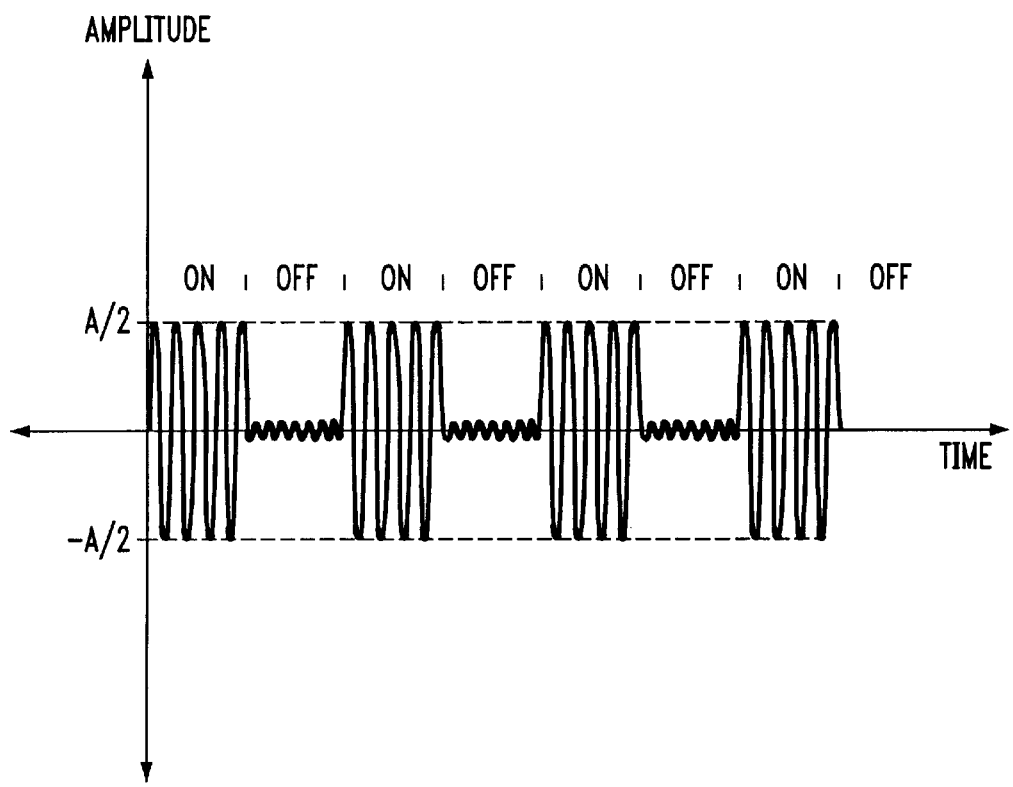
FIG. 2 is a graph showing a signal provided according to the present invention.

As shown in FIG. 2, the output signal from the signal generator 12 is representatively shown. As can be seen, a signal having an amplitude A is generated during "on" periods of the signal and a signal having substantially zero amplitude is generated during "off" periods. It is to be appreciated that the "on" and "off" periods of the signal occur at a substantially lower frequency than the high frequency signal (e.g. RF signal) that is being modulated. It is to be further appreciated that during the "on" period of the signal, as noted above, the cantilever arm 16 and tip 18 are essentially levitating because, as noted above, these devices are not mechanically able to follow the high frequency signal. Nonetheless, the amplitude of the deflection of the cantilever arm 16 and tip 18 is tracked by use of the AM signal shown as the tip moves in opposite vertical directions in response to the signal.

Referring back to FIG. 1, the signals from the detector 22 are sent to a lock-in amplifier 26 for phase-locked detection and/or synchronization. A feature of this arrangement is that it is a truly differential technique, since it measures point by point the amplitude of the vibration. This feature is essential in cases such as this where small amplitude vibrations (<1 Å) are to be measured over a relatively rough surface (~tens of Å). The synchronized signals are then sent to the processing element 28 to map a topography of the surface of the specimen 30 as it responds to the applied high frequency. This topography is also referred to as the RF topography.

In addition, the signals measured by the phase-locked loop, or lock-in amplifier, 26, and ultimately sent to processing element 28, are directly proportional to the amplitudes of the RF driving voltage, and independent of the modulation frequency (in the 2 KHz to 20 KHz range) and the pressure exerted by the tip 18 on the surface of the resonating specimen 30. Thus, this linear behavior allows for a precise calibration of the system and absolute measurements of the amplitude of motion of the device are obtained.

In this regard, the phase locked loop, or lock-in amplifier, measures a voltage that is proportional to the amplitude of the motion of the cantilever arm. This simple linear behavior can be calibrated against materials of known properties, and that calibration can ultimately be used to calculate the amplitude of vibration of materials or devices of unknown properties.

For example, as to the calibration, when considering the vertical deflection of the cantilever arm, a standard sample of PZT and a sample of LiNbO, two piezoelectric materials of known properties, are used. The calibration is as follows. Each of the standard samples is put into a vibrating state of known amplitude. The cantilever is brought in contact with the surface's sample and the voltage measured by the phase locked loop is recorded. Then, the voltage measured by the phase-locked loop is divided by the amplitude of vibration of the standard. As such, a calibration coefficient of the system is determined. In one case, 0.72 Å/mV was obtained. This means that, when considering a sample of unknown characteristics, each millivolt measured by the phase-locked loop corresponds to 0.72 Å of amplitude of vertical motion. This information can then be used to calculate the piezoelectric coefficient of a specimen where the amplitude of motion and output voltage are known, as described below.

Figure 3:
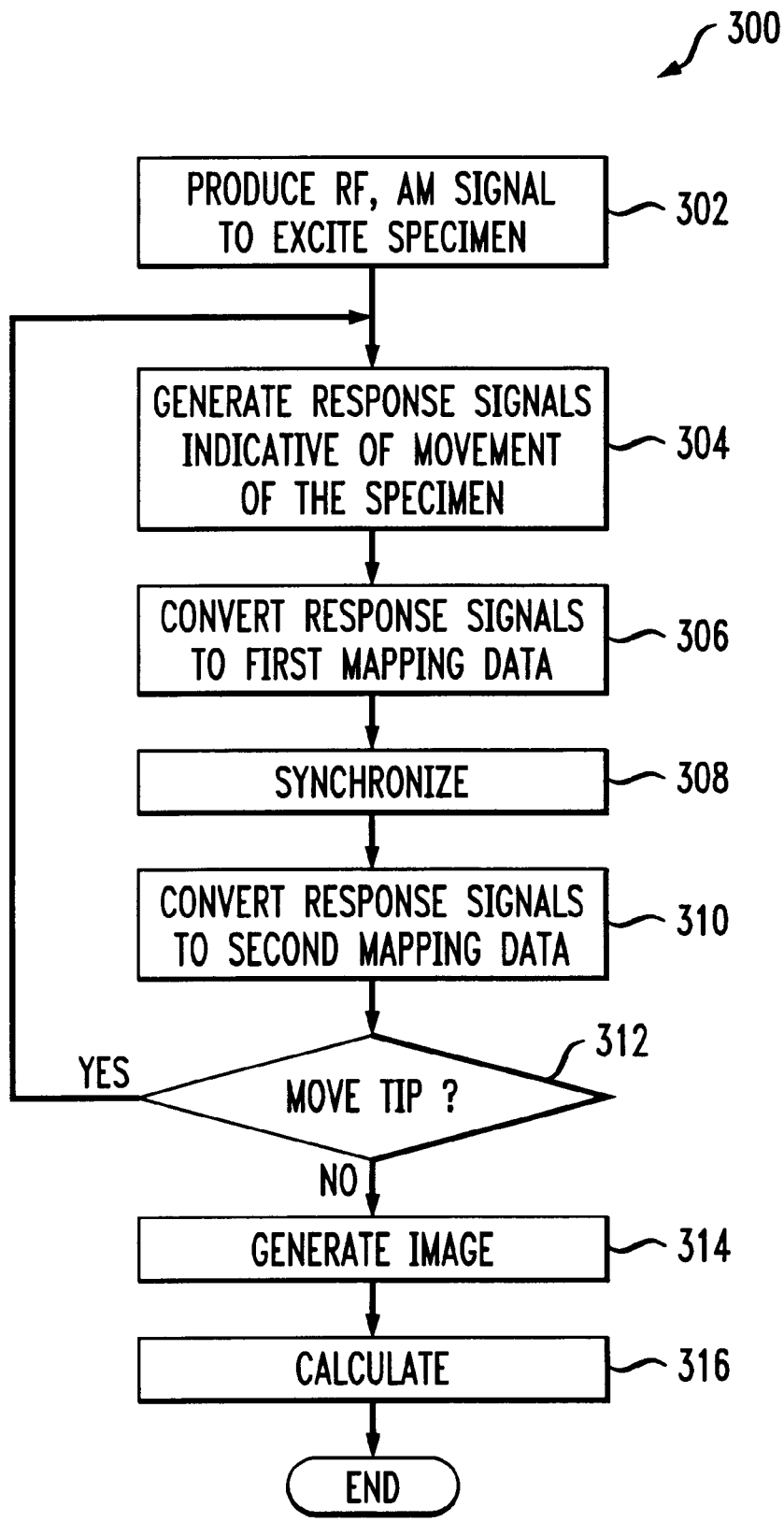
FIG. 3 is a flowchart illustrating a method according to the present invention.

A method of operation is illustrated in flow chart form in FIG. 3. It should be recognized that the method is implemented using techniques compatible with the system components described herein. As such, various hardware and software techniques that will be apparent to skilled artisans upon a reading of this disclosure may be implemented.

As shown, a method 300 is initiated by producing a radio frequency signal to excite a specimen 30 (step 302). The radio frequency signal that is generated, as noted above, has a first frequency that is amplitude modulated at a second frequency. Of course, the second frequency is less than the first frequency. A specimen is excited based on the signal produced by the generator 12 and the detector 22 generates detector, or response, signals indicating the movement of the specimen in response to the radio frequency signal produced by the signal generator 12 (step 304).

These response signals are then converted to first mapping data by the first processing element (step 306). The first mapping data relates to physical characteristics, such as surface typography, of the specimen. The response signals are also synchronized with the second frequency (step 308). The synchronized response signals are then converted to second mapping data by the second processing element (step 310). The second mapping data relates to response characteristics of the excited specimen.

A determination is then made whether the tip 18 of the cantilever arm 16 should be moved, or translated, to another location on the surface of the specimen (step 312). If so, steps 304 to 312 are repeated. If not, images are generated based on the first and second mapping data (step 314). Of course, it is to be appreciated that images (based on data obtained up to that point in time) may be generated before the determination is made whether to translate the tip 18. In either case, once sufficient data is collected, the piezoelectric coefficient can then be calculated based on the response signals (step 316). The process is then ended (step 318).

According to the present invention, the vertical vibration modes of a thinfilm resonator structure are mapped. The vertical motion of the cantilever arm (versus $LiNbO_3$ and PZT materials of known piezoelectric coefficients) is also calibrated as described above to obtain an absolute measurement of the specimen's vertical motion and piezoelectric coefficient. With this information, the AlN piezoelectric film used in the specimens was investigated and the piezoelectric coefficient value experimentally calculated to be equal to 0.030±0.05 Å/V at 10 MHz and equal to 0.030±0.05 A/V at 1 GHz. These results are comparable to the known dc value for bulk AlN of 0.05 Å/V. As such, coefficients relating to characteristics can be calculated based on the detector signals.

Figure 4A:
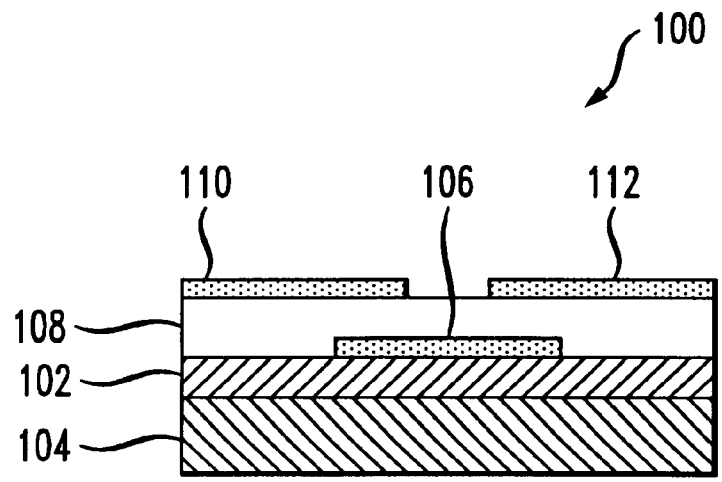
FIGS. 4(a) and (b) provide views of the geometry of an exemplary specimen analyzed according to the present invention; and, FIGS. 5(a) through (e) show the output of the system according to the present invention.

The mapping results of the present invention will be discussed in connection with FIGS. 5(a)–(e); however, the geometry of the specimen should be first considered. As such, a sketch of the geometry of an exemplary thin-film resonator (TFR device) 100 studied is shown in FIGS. 4(a) and (b). First, an acoustic mirror 102 comprising alternating layers of high and low acoustic impedance materials with quarter wavelength thickness is deposited over a silicon layer 104. A floating Al bottom electrode 106 is deposited on the acoustic mirror 102. An AlN piezoelectric layer 108 is later deposited over the bottom electrode. Finally, two top Al electrodes 110 and 112 are deposited onto the piezoelectric material.

The position of the top electrodes overlaps with the bottom electrode, giving an effective equivalent circuit of two resonators connected in series. For the data collection described here, one of the electrodes is connected to a RF source, the other is connected to ground through a 50 Ω termination. All experiments presented to obtain the results were performed imaging the amplitude of vertical vibration of one of the top electrodes of the specimen, while a RF voltage is applied between the electrodes. Electrical characterization of these devices was performed by standard 2-port analysis using a vector network analyzer. This characterization yielded information such as the zero and pole frequencies, Q values, insertion loss, etc. of the specimen.

Figure 4B:
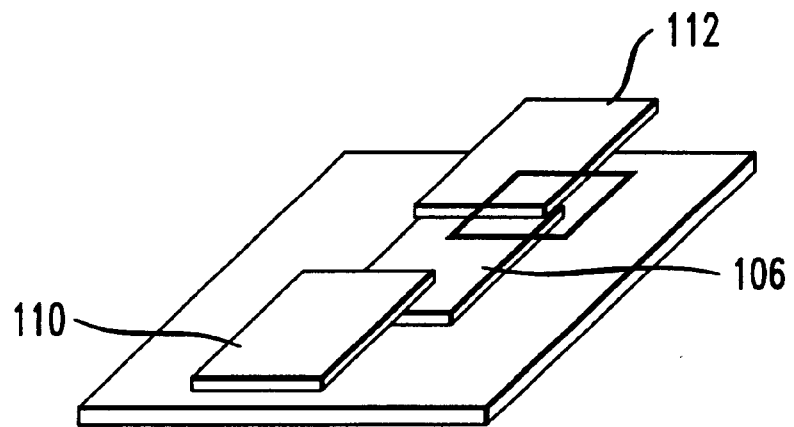

Referring now to FIGS. 5(a)–(e), images of a TFR device similar to that of FIGS. 4(a)–(b) in operation are shown. This particular device has square aluminum electrodes of 200×200 μm. Shown in the figure is a series of 50×50 μm images, taken at different frequencies, of the amplitude of oscillations near the corner of one of the top electrodes. These images were taken at a 512×512 pixels resolution, corresponding to a lateral resolution better than 0.1 μm.

Figure 5A:
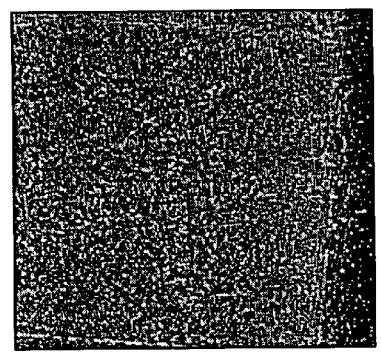
Figure 5B:
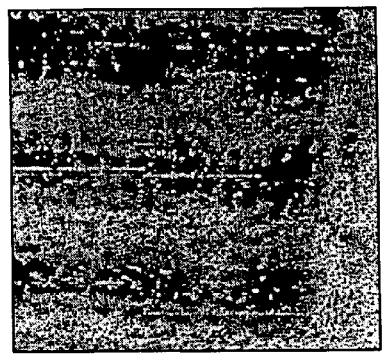
Figure 5C:
Figure 5D:
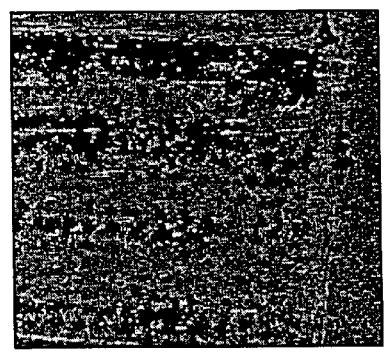

As shown in FIG. 5(a), at 2.09 GHz, the frequency of the zero of the device, a spatially uniform vibration of the electrode results. Most of this image is occupied by the top electrode, with the boundaries of the electrode being evident by straight lines (for example, in the right hand side of the image).

This "flat-plate" motion is experimentally observed over a wide frequency range, from 1 MHz up to the zero frequency, e.g. 2.09 GHz, and beyond the pole of the device up to the highest frequency investigated.

However, quite complex mode shapes, with strong deviations from the simple "flat plate" mode, are observed in the narrow frequency range between the zero (2.085 GHz) and the pole (2.140 GHz), and also slightly above the pole of the device. As seen in the figures, two very different features emerge in this frequency interval. On one hand, a short-scale structure, with a typical length of about 2–3 μm, is apparent. On the other hand, a large-scale mode is clearly seen. This large-scale mode has the same four-fold symmetry as the shape of the electrodes. As shown by the images taken at 2.14 GHz and 2.16 GHz (FIGS. 5(b) and (d)), the periodicity of this large-scale mode is seen to change rapidly with frequency, from 26 μm at 2.12 GHz to 11 μm at 2.16 GHz. The periodicity of the short-length mode does not change appreciably with frequency.

Figure 5E:
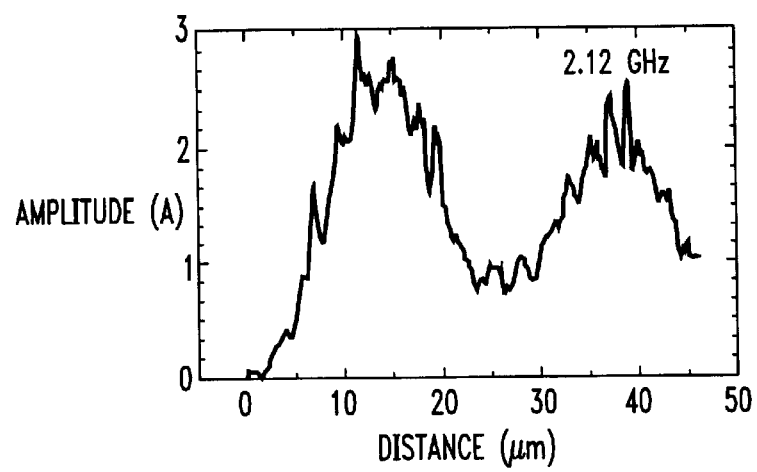

Shown in FIG. 5(e) is a cross-sectional plot of the amplitude of the vibration measured at 2.12 GHz. For this plot, the amplitude of vibration along the line L is shown in the image. The importance of the long-wavelength mode, which takes up most of the amplitude of the vibration, will be apparent to those skilled in the art. This vibration pattern will have an obvious effect on the electrical performance of the device, since, for example, different regions of the device will have a different piezoelectric moment.

A second interesting feature observed is the presence of a short-length structure of about 2.5 μgm of wavelength. Clearly, the superior lateral resolution of the present system is crucial for a distinctive detection of this short wavelength structure.

In the present invention, a technique capable of imaging the vibration modes of a new generation of high-frequency, bulk-mode piezoelectric resonators is shown. Among the advantages of this technique are its differential nature, allowing resolution of sub-angstrom vibrations over a nanometer-rough landscape, and outstanding lateral resolution. Combined, these features allow for mapping of the complex mode of vibration of bulk-mode thin film resonators operating well into the GHz range. The obtained data will aid in design and understanding of the origin of energy loss in bulk-mode piezoelectric resonators.

The above description merely provides a disclosure of particular embodiments of the invention and is not intended for the purposes of limiting the same thereto. As such, the invention is not limited to only the above described embodiments. Rather, it is recognized that one skilled in the art could conceive alternative embodiments that fall within the scope of the invention.

Having thus described the invention, we hereby claim:

1. An apparatus comprising:
    a cantilever arm having a tip disposed at an end thereof, the tip being positioned to engage a surface of a specimen;
    a detecting system positioned to detect motion of the cantilever arm and produce detector signals based on the motion;
    a frequency generator producing a radio frequency signal to excite the specimen, the radio frequency signal having a first frequency that is amplitude modulated at a second frequency, the second frequency being less than the first frequency;
    a circuit operatively connected between the detecting system and the frequency generator to synchronize the detector signals with the second frequency;
    a first processing element operatively connected to the detecting system to convert the detector signals to first mapping data, the first mapping data relating to physical characteristics of the specimen; and, a second processing element operatively connected to the detecting system to convert the detector signals to second mapping data, the second mapping data relating to response characteristics of the specimen excited by the first frequency.

2. The apparatus as set forth in claim 1 wherein the tip is translated across the surface of the specimen.

3. The apparatus as set forth in claim 1 wherein the first mapping data comprises data relating to a topography of the surface of the specimen.

4. The apparatus as set forth in claim 1 wherein the tip moves in opposite vertical directions in response to the radio frequency signal.

5. The apparatus as set forth in claim 1 wherein the second mapping data comprises data relating to amplitudes of the movement of the tip.

6. The apparatus as set forth in claim 1 wherein coefficients relating to characteristics of the specimen are calculated based on the detector signals.

7. The apparatus as set forth in claim 1 wherein the detecting system to detect comprises a laser light source positioned to direct a laser light beam toward the cantilever arm and a detector positioned to detect the laser light beam reflected from the cantilever arm and to produce the detector signals based on a position of the reflected beam on the detector.

8. An apparatus for determining characteristics of a specimen, the apparatus comprising:
 a means for producing a radio frequency signal to excite the specimen, the radio frequency signal having a first frequency that is amplitude modulated at a second frequency, the second frequency being less than the first frequency;
 a means for generating response signals indicative of movement of the specimen in response to the radio frequency signal;
 a means for synchronizing the response signals with the second frequency; and,
 a means for converting the synchronized response signals to mapping data, the mapping data relating to response characteristics of the specimen excited by the first frequency.

9. The apparatus as set forth in claim 8 further comprising a means for converting the response signals to additional mapping data, the additional mapping data relating to physical characteristics of the specimen.

10. The apparatus as set forth in claim 8 wherein the means for generating response signals comprises a means for generating a laser light beam.

11. The apparatus as set forth in claim 10 wherein the means for generating response signals further comprises a means for detecting the laser light beam reflected from the specimen.

12. The apparatus as set forth in claim 8 wherein the means for synchronizing comprises a lock-in circuit.

13. The apparatus as set forth in claim 8 wherein coefficients relating to characteristics of the specimen are calculated based on the response signals.

14. A method for determining characteristics of a specimen, the method comprising steps of:
 producing a radio frequency signal to excite the specimen, the radio frequency signal having a first frequency that is amplitude modulated at a second frequency, the second frequency being less than the first frequency;
 generating response signals indicative of movement of the specimen in response to the radio frequency signal;
 converting the response signals to first mapping data, the first mapping data relating to physical characteristics of the specimen;
 synchronizing the response signals with the second frequency; and,
 converting the synchronized response signals to second mapping data, the second mapping data relating to response characteristics of the specimen excited by the first frequency.

15. The method as set forth in claim 14 further comprising calculating coefficients relating to characteristics of the specimen based on the response signals.

* * * * *